United States Patent
Agustinos et al.

(10) Patent No.: US 12,082,896 B2
(45) Date of Patent: Sep. 10, 2024

(54) SURGICAL NAVIGATION SYSTEM ON WEARABLE COMPUTER COMBINING AUGMENTED REALITY AND ROBOTICS

(71) Applicant: PIXEE MEDICAL, Besançon (FR)

(72) Inventors: Anthony Agustinos, Devecey (FR); Quentin Lavenu, Besançon (FR); Luis Contreras, Besançon (FR)

(73) Assignee: PIXEE MEDICAL, Besançon (FR)

( * ) Notice: Subject to any disclaimer, the term of this patent is extended or adjusted under 35 U.S.C. 154(b) by 261 days.

(21) Appl. No.: 17/880,240

(22) Filed: Aug. 3, 2022

(65) Prior Publication Data
US 2023/0076894 A1    Mar. 9, 2023

Related U.S. Application Data

(60) Provisional application No. 63/229,312, filed on Aug. 4, 2021.

(51) Int. Cl.
*A61B 34/32*    (2016.01)
*A61B 34/10*    (2016.01)
(Continued)

(52) U.S. Cl.
CPC .............. *A61B 34/32* (2016.02); *A61B 34/10* (2016.02); *A61B 90/36* (2016.02);
(Continued)

(58) Field of Classification Search
CPC ......... A61B 34/32; A61B 34/10; A61B 90/36; A61B 2034/101; A61B 2034/107;
(Continued)

(56) References Cited

U.S. PATENT DOCUMENTS

| | | | | |
|---|---|---|---|---|
| 5,721,566 A | * | 2/1998 | Rosenberg | ............ G06F 3/0383 345/161 |
| 5,959,613 A | * | 9/1999 | Rosenberg | ............ A63F 13/285 345/157 |

(Continued)

OTHER PUBLICATIONS

Zimmer Biomet, "Rosa(R) Knee System", https://www.zimmerbiomet.com/en/products-and-solutions/specialties/knee/rosa--knee-system.html, visited Aug. 3, 2022 (total 13 pages).

(Continued)

*Primary Examiner* — Bhavesh V Amin
(74) *Attorney, Agent, or Firm* — Seckel IP, PLLC

(57) ABSTRACT

The system for assisting a surgeon in the context of surgical operations includes a mobile wearable computer worn or carried by a user of the system, at least one perception sensor for collecting anatomical and/or instrumental measurement data in an operating scene, a processor adapted to process the collected anatomical and/or instrumental measurement data collected by the at least one perception sensor, a memory connected to the processor and adapted to store anatomical and/or instrumental measurement data, a robotic effector connected to the processor and adapted to carrying an instrument, wherein movements of the robotic effector are slaved to the anatomical and/or instrumental measurement data, wherein the anatomical and/or instrumental data delimit an area of action within which the movements of the robotic arm are restricted in the operating scene.

20 Claims, 2 Drawing Sheets

(51) Int. Cl.
*A61B 34/20* (2016.01)
*A61B 34/30* (2016.01)
*A61B 90/00* (2016.01)

(52) U.S. Cl.
CPC ... *A61B 2034/101* (2016.02); *A61B 2034/107* (2016.02); *A61B 2034/2055* (2016.02); *A61B 2034/2068* (2016.02); *A61B 2034/305* (2016.02); *A61B 2090/365* (2016.02)

(58) Field of Classification Search
CPC .... A61B 2034/2055; A61B 2034/2068; A61B 2034/305; A61B 2090/365; A61B 34/20; A61B 34/37; A61B 2034/105; A61B 2034/2057; A61B 2034/2065; A61B 2090/372; A61B 2090/502
See application file for complete search history.

(56) References Cited

U.S. PATENT DOCUMENTS

| | | | | |
|---|---|---|---|---|
| 6,020,876 A * | 2/2000 | Rosenberg | ............ | G06F 3/016 345/157 |
| 7,056,123 B2 * | 6/2006 | Gregorio | ............ | A61B 34/71 434/262 |
| 7,155,316 B2 * | 12/2006 | Sutherland | ............ | A61B 34/37 901/1 |
| 7,404,716 B2 * | 7/2008 | Gregorio | ............ | G09B 23/285 434/262 |
| 7,660,623 B2 * | 2/2010 | Hunter | ............ | A61B 17/1703 345/418 |
| 8,831,779 B2 * | 9/2014 | Ortmaier | ............ | G05B 19/4061 318/590 |
| 9,060,796 B2 * | 6/2015 | Seo | ............ | A61B 34/77 |
| 9,220,570 B2 * | 12/2015 | Kim | ............ | A61B 34/76 |
| 9,480,534 B2 * | 11/2016 | Bowling | ............ | A61B 34/30 |
| 9,539,726 B2 * | 1/2017 | Simaan | ............ | A61B 34/35 |
| 9,566,121 B2 * | 2/2017 | Staunton | ............ | A61B 17/32002 |
| 9,630,323 B2 * | 4/2017 | Kishi | ............ | B25J 9/1643 |
| 9,937,014 B2 * | 4/2018 | Bowling | ............ | A61B 34/32 |
| 9,956,042 B2 * | 5/2018 | Simaan | ............ | A61B 34/74 |
| 10,034,675 B2 * | 7/2018 | Pack | ............ | A61B 17/1714 |
| 10,251,708 B2 * | 4/2019 | Cho | ............ | G06N 3/008 |
| 10,350,017 B2 * | 7/2019 | Bowling | ............ | B25J 9/161 |
| 10,390,890 B2 * | 8/2019 | Jagga | ............ | A61B 34/25 |
| 10,420,619 B2 * | 9/2019 | Bowling | ............ | A61B 34/37 |
| 10,463,440 B2 * | 11/2019 | Bowling | ............ | A61B 34/37 |
| 10,695,134 B2 * | 6/2020 | Barral | ............ | B25J 9/1633 |
| 10,806,527 B2 * | 10/2020 | Bar | ............ | A61B 90/06 |
| 11,033,296 B2 * | 6/2021 | Carlson | ............ | A61B 5/061 |
| 11,045,958 B2 * | 6/2021 | Bowling | ............ | B25J 9/161 |
| 11,471,232 B2 * | 10/2022 | Bowling | ............ | A61B 34/70 |
| 11,750,794 B2 * | 9/2023 | Benishti | ............ | H04N 13/344 345/592 |
| 11,766,296 B2 * | 9/2023 | Wolf | ............ | G02B 27/0093 600/424 |
| 11,801,115 B2 * | 10/2023 | Elimelech | ............ | A61B 90/361 |
| 11,896,445 B2 * | 2/2024 | Gera | ............ | A61B 90/37 |
| 11,911,277 B2 * | 2/2024 | Ratron | ............ | A61B 90/36 |
| 11,974,887 B2 * | 5/2024 | Elimelech | ............ | A61B 90/39 |
| 11,980,429 B2 * | 5/2024 | Wolf | ............ | G02B 27/0093 |
| 11,980,506 B2 * | 5/2024 | Wolf | ............ | A61B 90/39 |
| 2005/0162383 A1 * | 7/2005 | Rosenberg | ............ | G06F 3/03545 345/156 |
| 2006/0261770 A1 * | 11/2006 | Kishi | ............ | B25J 9/1676 318/568.11 |
| 2007/0171200 A1 * | 7/2007 | Rosenberg | ............ | G05B 19/409 345/156 |
| 2009/0037033 A1 * | 2/2009 | Phillips | ............ | G06F 9/451 701/2 |
| 2009/0088774 A1 * | 4/2009 | Swarup | ............ | A61B 34/37 901/31 |
| 2010/0331855 A1 * | 12/2010 | Zhao | ............ | A61B 34/30 606/130 |
| 2010/0331859 A1 * | 12/2010 | Omori | ............ | A61B 34/37 606/130 |
| 2011/0015649 A1 * | 1/2011 | Anvari | ............ | A61B 34/20 606/130 |
| 2011/0130761 A1 * | 6/2011 | Plaskos | ............ | A61B 34/10 606/87 |
| 2011/0152676 A1 * | 6/2011 | Groszmann | ............ | A61B 6/12 600/426 |
| 2011/0208256 A1 * | 8/2011 | Zuhars | ............ | A61F 2/30942 606/86 R |
| 2011/0263971 A1 * | 10/2011 | Nikou | ............ | A61B 90/39 600/424 |
| 2011/0264107 A1 * | 10/2011 | Nikou | ............ | A61B 17/1633 700/258 |
| 2011/0301500 A1 * | 12/2011 | Maguire | ............ | A61B 34/76 600/583 |
| 2012/0053597 A1 * | 3/2012 | Anvari | ............ | B25J 9/1689 606/130 |
| 2012/0059378 A1 * | 3/2012 | Farrell | ............ | A61B 90/25 606/80 |
| 2012/0071752 A1 * | 3/2012 | Sewell | ............ | A61B 34/74 345/650 |
| 2012/0071893 A1 * | 3/2012 | Smith | ............ | A61B 17/1666 606/130 |
| 2012/0083801 A1 * | 4/2012 | Nixon | ............ | B25J 9/1692 700/254 |
| 2013/0325029 A1 * | 12/2013 | Hourtash | ............ | B25J 9/1607 606/130 |
| 2013/0345718 A1 * | 12/2013 | Crawford | ............ | A61B 90/39 606/130 |
| 2014/0039517 A1 * | 2/2014 | Bowling | ............ | A61B 34/70 606/130 |
| 2014/0039681 A1 * | 2/2014 | Bowling | ............ | A61B 34/30 700/261 |
| 2014/0052153 A1 * | 2/2014 | Griffiths | ............ | A61B 34/30 606/130 |
| 2014/0135795 A1 * | 5/2014 | Yanagihara | ............ | A61B 17/32002 606/130 |
| 2014/0148818 A1 * | 5/2014 | Komuro | ............ | A61B 46/10 606/130 |
| 2014/0222207 A1 * | 8/2014 | Bowling | ............ | A61B 34/30 700/261 |
| 2014/0276952 A1 * | 9/2014 | Hourtash | ............ | B25J 18/007 700/263 |
| 2014/0277742 A1 * | 9/2014 | Wells | ............ | B25J 9/1612 700/264 |
| 2014/0350571 A1 | 11/2014 | Maillet et al. | | |
| 2014/0378999 A1 * | 12/2014 | Crawford | ............ | A61B 17/1757 606/130 |
| 2015/0032164 A1 * | 1/2015 | Crawford | ............ | A61B 17/7074 606/279 |
| 2015/0081098 A1 * | 3/2015 | Kogan | ............ | B25J 13/085 901/46 |
| 2018/0071026 A1 * | 3/2018 | Malackowski | ............ | A61B 34/37 |
| 2021/0169605 A1 * | 6/2021 | Calloway | ............ | A61B 90/36 |
| 2023/0076894 A1 * | 3/2023 | Agustinos | ............ | A61B 34/10 |

OTHER PUBLICATIONS

Stryker, "Mako SmartRobotics Overview", https://www.stryker.com/us/en/joint-replacement/systems/Mako_SmartRobotics_Overview.html#know-more, visited Aug. 3, 2022 (total 6 pages).

* cited by examiner

SURGICAL NAVIGATION SYSTEM ON WEARABLE COMPUTER COMBINING AUGMENTED REALITY AND ROBOTICS

RELATED APPLICATION

This application claims priority of provisional application No. 63/229,312 filed Aug. 4, 2021, whose content is hereby incorporated by reference herein in its entirety.

FIELD OF THE INVENTION

The field of the invention is the use of augmented reality in surgery. More particularly, the present invention can be applied to navigation systems using augmented reality with a servo-controlled robotic arm in order to improve the precision of surgical gestures.

BACKGROUND ART

Robotic-based navigation systems for orthopedics currently available on the market are bulky setups that require a huge robotic arm unit, a cumbersome station composed of one or more viewing screens and a perception system generally of the infrared stereoscopic camera type.

The visualization of information useful to the surgeon, such as position and orientation measurements, operative data, is performed on a remote screen. The surgeon's attention is therefore focused on this screen rather than on the real scene, which can disturb the surgeon, complicate his gestures and require an adaptation of his practice compared to more conventional techniques. Moreover, the perception of the three dimensions of a scene can be difficult on a 2D screen, whereas it is essential for the precision of surgical gestures, for example the good orientation of prosthetic components, on which the success of an operation depends.

SUMMARY OF THE INVENTION

In one aspect of the present invention, an augmented reality system includes the use of a wearable mobile computing device. Perception sensors can be used to detect anatomical and/or instrument data in the surgical scene. A display component can overlay useful information in the surgeon's field of vision.

In another aspect, a wearable computer is connected to a robotic effector, such as a robotic arm which may carry an instrument, to assist the surgeon in performing some of the gestures of the surgical technique.

In another aspect, a wearable computer is equipped with a perception device, advantageously adapted for visual perception, typically one or a plurality of optical sensors, such as one or more cameras, which may each be secured to the wearable computer or to a different support. Sensors of various technologies can be used, such as RGB camera, infrared camera, monochrome camera, stereovision system by passive or active camera, LiDAR, RADAR, ultrasound devices, etc. A single sensor can be used, or a plurality of sensors using the same or different technologies.

In another aspect, the wearable computer is mobile and adapted to be worn or carried on the user's head, for example, in the form of or including smart glasses. 3D models of anatomical and/or instrumental components may be shown by the display component, alone or in superposition with a view of at least a portion of the surgical scene, which may be an image or a 3D model of at least a portion of the surgical scene.

In another aspect, the robotic effector is controlled to be constrained in displacement in the operating scene accordance with rules or restrictions based on the anatomical and/or instrument data acquired by the perception sensors. Movements of the robotic effector can be slaved to the anatomical and/or instrumental data, so as to delimit an area of action within which the movements of the robotic arm can be restricted.

In another aspect, a program for controlling the system can be stored on a non-transitory computer-readable data storage medium, such as a memory of the system.

A system according to the invention can be used, for example, in the context of total or partial knee replacement surgery, where certain practical imprecisions may cause the femoral and tibial components orientations to differ from the values initially planned by the surgeon, such as incidence angles, hold of the tool, fixation of the instruments, etc. A robotic arm can assist in achieving optimal control of such orientations, which depend on the precision of the cuts performed on the patient's bones. An augmented reality system can assist in determining or approximating the values planned by the surgeon pre-operatively. Sensor(s) can complement measurement made by a perception device of an augmented reality system.

In at least some embodiments, a system combines the qualities of the robotic arm with the small size of a portable navigation system that relies on augmented reality, offering the surgeon an improved visualization of the information and assistance in controlling the robotic arm. At least one processor, at least one memory, or both are included in the wearable computer or hosted in a separate component of the system, such as a station carrying the robotic effector, or an additional device, such as a controller of the system.

In at least some embodiments, some measurements, or even all measurements, are carried out by the perception system of the wearable computer using markers present on the instrumentation and the patient's bones.

BRIEF DESCRIPTION OF THE DRAWINGS

Further aspects of the invention will be described in reference to the appended drawings which illustrate non-limiting exemplary embodiments, and among which.

DETAILED DESCRIPTION OF PARTICULAR EMBODIMENTS

In a surgical operation using a robot, in order to be able to control the robot effectively, it is advantageous to provide constraints to guide the gesture of the surgeon. To this effect, it is necessary to locate the robot and in particular its effector, e.g., a robotic arm, such as an articulated robotic arm, possibly including an instrument carried by the robotic arm, in the reference frame of the perception system of the wearable computer.

For this purpose, at least one marker detectable by the perception system can be positioned on the robot. For example, a marker can be positioned on the effector, such as at the tip of a robotic arm.

Figure 1:
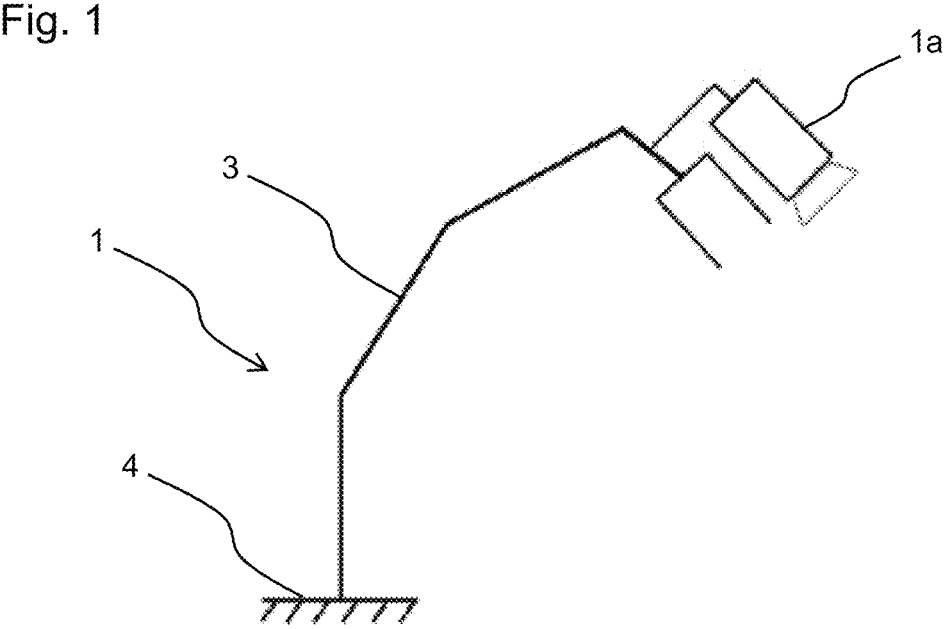
FIG. 1 is a schematic view of a first embodiment of an eye-in-hand visual servo system on a robotic arm.

As shown in FIG. 1, a camera 1a can be disposed on an effector of a robot 2, for example, by being fixed directly on a robotic arm 3 mounted on a base 4 of the robot 2 (so-called "eye-in-hand" configuration).

Figure 2:
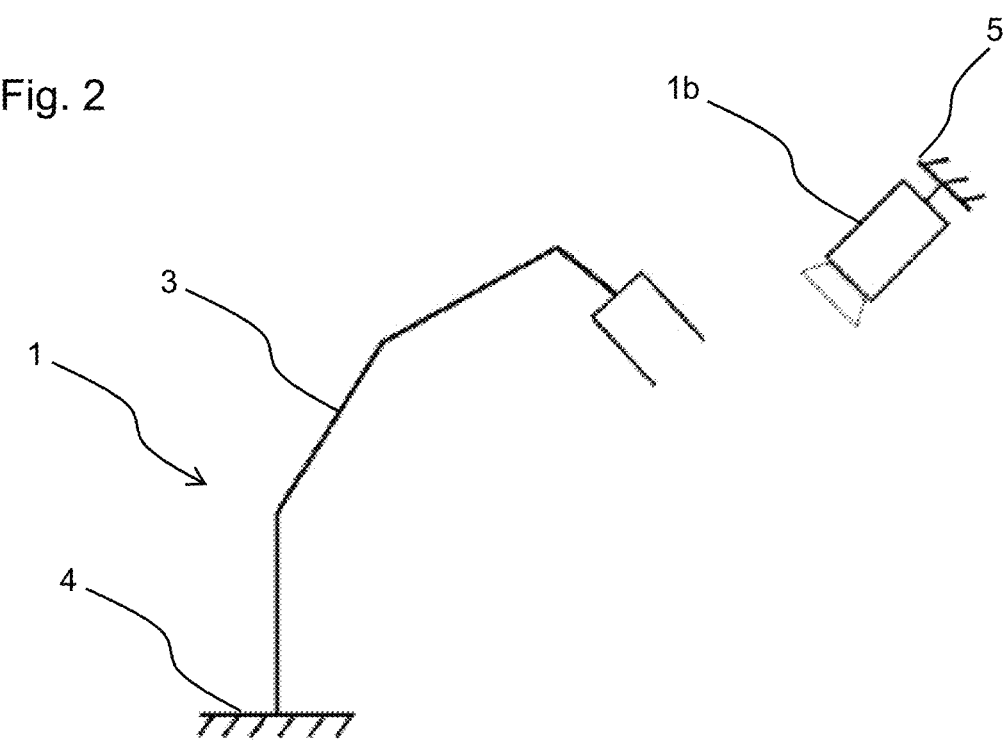
FIG. 2 is a schematic view of a second embodiment of an eye-to-hand visual servo system on a robotic arm.

Alternatively, or additionally, as shown in FIG. 2, a camera 1b can be disposed on a different support 5, which can be another portion of the robot, such as a base of the robot, a separate support structure, or a temporary or permanent fixed structure of the room in which the robot is intended to be used, such as a wall. In that case, a marker can be used which is fixed on the base of the robot which can be fixed. The location of the effector in the camera reference frame can be obtained using a geometric model of the robot (so-called "eye-to-hand" configuration). This way, the effector can be located, without the risk that a marker placed on the tip of a robotic arm, for example, would leave the field of view of the camera.

In still another embodiment, the effector is associated with at least two cameras synchronized with the perception system. In this configuration, the localization of the robot's effector in the 3D reference frame of the cameras can be obtained by matching visual primitives in the images coming from the at least two cameras, in an approach similar to stereoscopy. In this embodiment, the cameras may include a first camera 1a mounted on the effector, as shown in FIG. 1, or two or more such cameras, and a second camera 1b mounted on a different support, as shown in FIG. 2, or two or more such cameras. A system according to the invention may make successive or simultaneous use of an eye-in-hand, eye-to-hand, or stereoscopy-analogous locating techniques as described above.

The measurements thus taken make it possible to define anatomical landmarks on the patient's anatomy in the 3D surgical scene. The robotic arm can then navigate through the surgical scene and models created by these measurements.

The robot's effector can accommodate different instruments depending on the type of acquisition and the stage of surgery. The tools can be provided on the effector successively or together, for successive or simultaneous use. For example, for the modeling of a bone surface, such as the acquisition of a points cloud and registration with the 3D model of the patient, or for the acquisition of anatomical landmarks, a pointer-type instrument can be used.

Alternatively, additionally, or complementarily, the acquisition of the points cloud can be based on the data generated by a depth perception device, such as a LIDAR or a RGBD camera, advantageously installed on the robot's effector, for example, like other surgical tools.

In the context of surgery, particularly knee surgery, a robotic saw can be attached to the robot's effector and navigated by the wearable computer to assist the surgeon's gesture in performing cuts, such as a cut of the femur and/or of the tibia in knee surgery. For shoulder surgery, a pin or a drill can be attached to the robot's effector and navigated via the wearable computer to assist the surgeon's action in drilling the glenoid, for example.

The robotic arm is manipulated by the surgeon to perform the desired operation(s), such as cutting or drilling. The data acquired via the perception system and the planning defined by the surgeon make it possible to delimit one or more cutting or drilling area, if desired. The coordinates obtained constrain the movement of the robotic arm in space for the surgical gesture, setting a framework outside of which robot interventions are not possible.

Movements of the robot can be fully controlled by the system in accordance with predetermined parameters, or they can be co-manipulated by the surgeon. For example, the movements of the robot can accompany movements of the surgeon when the latter is in the cutting zone, and constrain him if he moves away from it.

A control of the robotic arm using the position of the robot and the patient's bones is calculated thanks to the measurements of the perception system, making it possible to determine the action to be carried out. In a particular embodiment, the system control of the movements can be deactivated temporarily or permanently, during which time the effector can be freely controlled and manipulated only by the surgeon.

Figure 3:
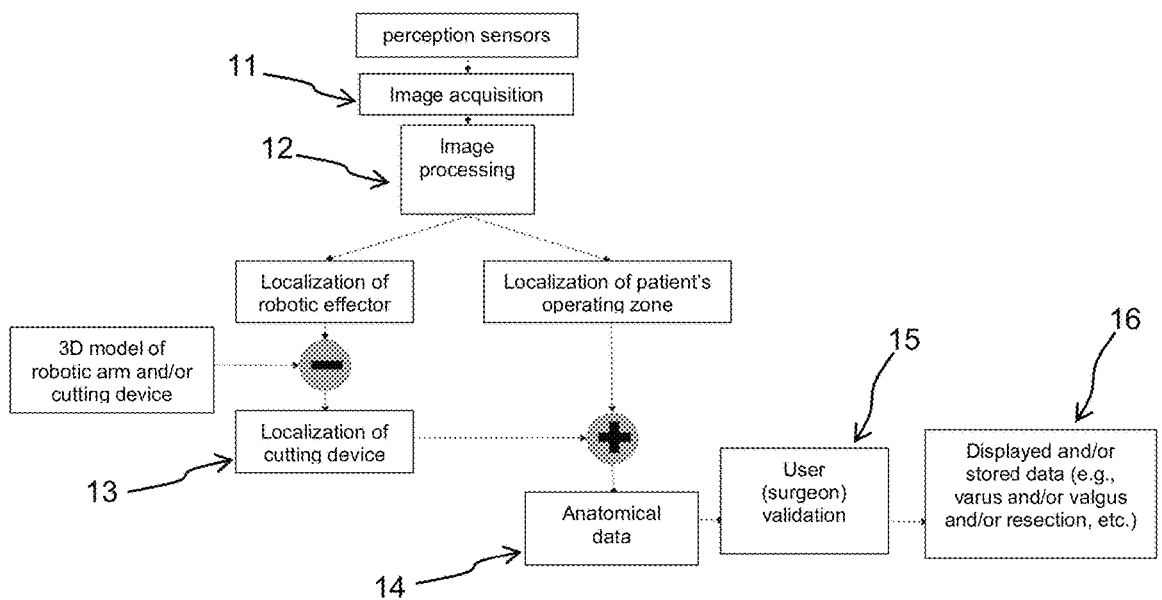
FIG. 3 is a flow chart illustrating the operation of an exemplary system comprising a robotic arm and virtual reality glasses according to the present invention.

FIG. 3 shows an implementation of an exemplary system of the present invention comprising a robotic arm adapted to carry a tool for knee surgery.

In a first stage 11, visual sensors, such as cameras 1a, 1b, etc., are used to capture images i) of the robot or portions of the robot, such as all or part of the robotic arm, and ii) of the patient or portions of the patient, such as all or part of the operation zone of the patient. Reference markers can be used or not. The reference markers, if used, can be placed on the robot and/or on the patient. Thus, the images may include visual reference markers or no visual reference markers.

In a second stage 12, the images are processed to obtain 1) a localization of the robot, and advantageously, more precisely a location of the robotic arm and/or a localization of a surgical tool carried by the robotic arm, and ii) a localization of the patient's bones, and advantageously, more precisely of an operation area of the patient.

As indicated above, the localization of the robotic effector can be obtained on the basis of a geometric and/or cinematic model of the robot and/or of the robotic arm and/or of the surgical tool, preferably via 3D model(s).

Thus, in a further stage 13, based on the localization of the robotic effector, a localization of the surgical tool can be obtained, optionally using a geometric and/or cinematic model of the robot and/or of the robotic arm and/or of the surgical tool, preferably via 3D model(s).

In a next stage 14, a set of anatomical values are obtained, based on the localization of the patient's bones and optionally of the cutting instrument.

Next, in a stage 15, the anatomical values can be validated by the user, typically the surgeon. For example, the values are shown to the surgeon via the augmented reality display of the wearable computer worn by the surgeon. The surgeon then validates the values, for example, by pressing a key or button, or by performing a predetermined movement or providing another visual or vocal instruction detectable by the system.

Optionally, the system then is adapted to provide or to store in one or more memories anatomical values useful to the surgery, such as varus and/or valgus, resection data, etc., as shown by stage 16 on FIG. 3.

Depending on the type of robot used, several surgical assistance options can be offered to the surgeon. For example, in the context of surgery including cutting bone, such as partial or total knee surgery:

The robot can be equipped with a cutting guide (a metal block with a thin slot), in which case the robot is automatically positioned in front of the patient's bones according to the steps of the operating protocol. The surgeon then performs the bone cut by manipulating an oscillating saw whose blade is guided by the position of the robot cutting guide.

The robot is directly equipped with a motor with an oscillating saw blade, in which case the robot is co-manipulated by the surgeon who is then free to move the instrument at the end of the robotic arm, but constrained in the cutting plane defined during the operating protocol.

The surgical gesture can be carried out with precision on the patient's bone, even if it is in motion because the perception system permanently locates the instruments and the bone structures, which allows real-time servoing of the robot with respect to defined cutting planes.

Figure 4:
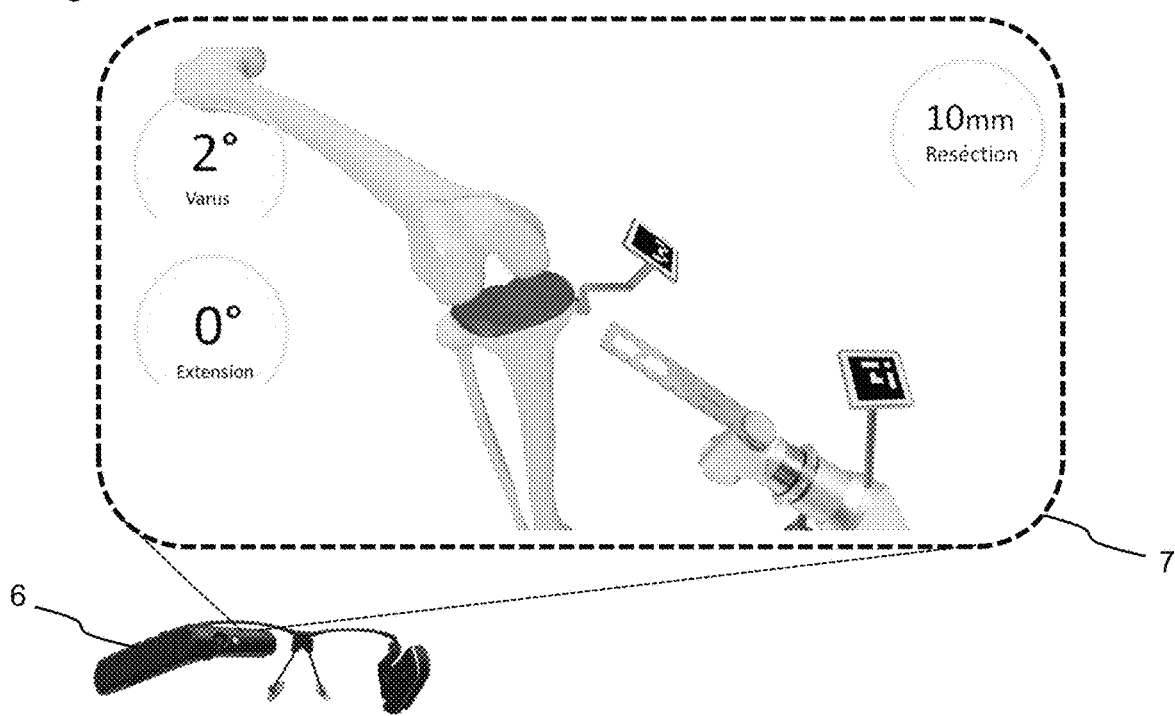
FIG. 4 is a perspective view of a robotic arm carrying a surgical tool controlled for performing a tibial cut of a knee surgery in an exemplary system according to the present invention.

FIG. 4 illustrates the use of a robotic arm carrying a surgical saw controlled for performing a tibial cut of a knee surgery in an exemplary system according to the present invention. The wearable computer 6, such as smart glasses worn by the surgeon, shows on its display, symbolically represented by the frame 7, a perspective view of the operating area, with the femur and the tibia. Markers detectable by the perception system are placed in the operating area and on the robotic arm, respectively. As a result of a data capture and processing as described above in reference to FIG. 3, the augmented reality display shows varus, extension and resection values superimposed with the perspective view of the operating scene. An augmented reality 3D model of the bones or portions of the bones can also be superimposed on the view of the operating area of the patient. This way, the surgeon has improved vision and information to assist in performing the cut, via movements of the robotic arm controlled by the system, co-manipulated by the surgeon, or entirely manipulated by the surgeon, possibly with limits fixed by the system, as described above.

In this example, the oscillating saw shown on FIG. 4 is controlled in the cutting plane in real time thanks to the spatial localization allowed by the markers.

The combination of augmented reality visualization and robotic assistance provides additional safety to the surgeon as the system can display critical areas related to the robot's movements directly in the surgical scene, present the surgeon with virtual control elements displayed directly on the robot, and display "transparently" through the patient's soft tissues instruments that would normally be hidden to prevent the risk of injury (rupture of a ligament, nerve or artery, for example).

In a variant embodiment, the use of markers is avoided, in that spatial localization is obtained based on 3D models of anatomical features and/or measuring and/or surgical instruments. This approach makes it possible to locate specific objects in the space of the operating scene, for example, anatomical surfaces such as articular surfaces, instruments such as those carried by the robotic arm, etc., as well as the position of the camera itself in the space of the operating scene based solely on their geometric and/or cinematic characteristics.

In another variant embodiment, the robotic arm is also used to carry out acquisitions, making it possible to digitize reference points and articular surfaces on the patient's bones. This is made possible by the installation of appropriate instruments at the end of the robotic arm, such as a probe or an active sensor of the 3D scanner type. The robot's internal localization system can be used. A potential advantage of this embodiment is the possibility of bringing the instrument very close to the measured zone. Another potential advantage is the possibility of visualizing directly on the surface of the patient's bone the joint areas already digitized and those still to be acquired, or of indicating by visual indicators the level of detail or precision of the acquired surfaces. Another advantage is to avoid the occlusion of the markers installed on the patient's bones and surgical instruments from the perception system, which can occur often during the surgical protocol.

Of course, the principle of a navigation system coupling augmented reality and a robotic arm can be applied to other operating contexts, for example to other joints: shoulder, hip, etc., according to the same principles as those previously defined for surgery of the knee. For example, in various applications, the system can be used to assist a surgeon in drilling and/or cutting bones for which the orientation of prosthetic components represents a challenge, for example, narrow approach, bulky soft tissues, hidden bone structure, etc.

Augmented reality makes it possible to display virtual information in the operating scene directly in the surgeon's field of vision, either superimposed on the reality perceived by the surgeon ("mixed reality" vision) or superimposed on a video stream displayed in his field of vision ("augmented reality" vision). The robotic arm makes it possible to reduce inaccuracies induced during the manipulation of the instruments by the surgeon, and/or to guide his gesture through co-manipulation constraints. The combination of augmented reality visualization and robotic guidance can provide additional safety to the surgeon because the system can display critical areas related to robot movements directly in the operating scene, and/or present the surgeon with virtual control elements displayed directly on the robot, and/or display in "transparency" through the patient's soft tissues instruments that would normally be hidden to prevent the risk of injuring the patient, such as through rupture of a ligament, nerve or artery, for example.

Thus, a major potential advantage of this navigation solution compared to existing systems lies in the combination of advantages of augmented reality and of robotics, as described above. For example, the system can integrate augmented reality glasses by Vuzix, Rochester, NY, for example, a model M400, which will cooperate with robot effectors from various manufacturers, such as Stäubli, Pfäffikon (Switzerland).

The augmented reality display can be a single 2D image view with superposed information, or an actual 3D view by the eye of the user, with superposed stereoscopic information provided by the device, or even a virtual simulation of an actual view with superposed information, or any combination of these augmented reality displays. The virtual simulation of an actual view can be created based on an actual view, on a model, such as a 2D or 3D model, of the actual view, from a predefined model, such as a 2D or 3D model, or any combination of these simulations. A portion of an actual view or of an image of an actual view may be excluded or occluded in favor of the augmented reality information, such as by framing and/or covering.

The above disclosures, embodiments and examples are nonlimitative and for illustrative purposes only.

The invention claimed is:

1. A system for assisting a surgeon in the context of surgical operations, the system comprising:
   a mobile wearable computer adapted to be worn or carried by a user of the system,
   at least one perception sensor for collecting anatomical and/or instrumental measurement data in an operating scene,
   a processor adapted to process the collected anatomical and/or instrumental measurement data collected by the at least one perception sensor, a memory connected to the processor and adapted to store anatomical and/or instrumental measurement data, a robotic effector connected to the wearable computer and adapted to carrying an instrument, wherein the wearable computer is connected to the at least one perception sensor, to the memory, and to the processor, and wherein movements of the robotic effector are slaved to the anatomical and/or instrumental measurement data, wherein the anatomical and/or instrumental data delimit an area of action within which the movements of the robotic arm are restricted in the operating scene.

2. The system according to claim 1, wherein the wearable computer is smart glasses.

3. The system according to claim 1, wherein the robotic effector is an articulated robotic arm.

4. The system according to claim 1, wherein the robotic arm carries a surgical instrument.

5. The system according to claim 1, wherein the at least one perception sensor includes at least one camera.

6. The system according to claim 1, wherein the anatomical and/or instrumental measurement data collected by the at least one sensor includes geometric data obtained via at least two markers implanted in the surgical scene.

7. The system according to claim 6, wherein the geometric data is obtained by the at least one perception sensor from visual data including at least one marker identified by a visual code.

8. The system according to claim 6, wherein the geometric data includes position and/or orientation values.

9. The system according to claim 6, wherein anatomical and/or instrumental resulting from processing the anatomical and/or instrumental measurement data obtained via the at least two markers is displayed by the wearable computer in superposition with a view of at least a portion of the operating scene.

10. The system according to claim 9, wherein the view of the at least a portion of the operating scene is an image of the at least a portion of the operating scene.

11. The system according to claim 9, wherein the view of the at least a portion of the operating scene includes a 3D model of the at least a portion of the operating scene.

12. The system according to claim 9, wherein the view of the at least a portion of the operating scene is a 3D model of the at least a portion of the operating scene.

13. The system according to claim 9, wherein the view of the at least a portion of the operating scene is the user's vision augmented by virtual information and 3D model(s).

14. The system according to claim 1, wherein the movements of the robotic effector are adapted to be co-manipulated by the user of the system within the area of action.

15. The system according to claim 1, wherein spatial localization of anatomical and/or instrument components is obtained based on 3D models of the components.

16. The system according to claim 15, wherein spatial localization of anatomical and/or instrument components is obtained without relying on data acquired from markers positioned in the operating scene.

17. The system according to claim 1, wherein the robotic effector carries at least one perception sensor connected to the processor.

18. The system according to claim 1, wherein the wearable computer displays a digitized 3D model of an anatomical surface.

19. A non-transitory computer-readable data storage medium on which is stored program comprising navigation instructions for controlling a system for assisting a surgeon in the context of surgical operations, the system comprising:

a mobile wearable computer adapted to be worn or carried by a user of the system, at least one perception sensor for collecting anatomical and/or instrumental measurement data in an operating scene, a processor adapted to process the collected anatomical and/or instrumental measurement data collected by the at least one perception sensor, a memory connected to the processor and adapted to store anatomical and/or instrumental measurement data, a robotic effector connected to the processor and adapted to carrying an instrument, wherein the wearable computer is connected to the at least one perception sensor and to the memory, wherein the program is adapted, when the program is run on a computer, to control an operation of the system to implement a slaving of the movements of the robotic effector to the anatomical and/or instrumental measurement data, wherein the anatomical and/or instrumental data delimit an area of action within which the movements of the robotic arm are restricted in the operating scene.

20. A method of assisting a surgeon in the context of surgical operations, the method comprising:

providing at least one perception sensor for collecting anatomical and/or instrumental measurement data in an operating scene, collecting anatomical and/or instrumental measurement data in an operating scene, processing the collected anatomical and/or instrumental measurement data collected by the at least one perception sensor, providing a robotic effector adapted to carrying an instrument, slaving movements of the robotic effector to the anatomical and/or instrumental measurement data, wherein the anatomical and/or instrumental data delimit an area of action within which the movements of the robotic arm are restricted in the operating scene, providing a mobile wearable computer adapted to be worn or carried by a user of the system, and displaying information obtained from the processing on the mobile wearable computer adapted to be worn or carried by a user of the system.

* * * * *